(12) United States Patent
Abrahamson et al.

(10) Patent No.: US 10,689,675 B2
(45) Date of Patent: Jun. 23, 2020

(54) ENZYMATIC PROCESSES FOR THE PREPARATION OF (±)-2-(DIFLUOROMETHYL)-1-(ALKOXYCARBONYL)-CYCLOPROPANECARBOXYLIC ACID AND (±)-2- (VINYL)-1-(ALKOXYCARBONYL)-CYCLOPROPANECARBOXYLIC ACID

(71) Applicant: AbbVie Inc., North Chicago, IL (US)

(72) Inventors: Michael J. Abrahamson, Chicago, IL (US); Sanjay R. Chemburkar, Gurnee, IL (US); Angelica B. Kielbus, Evanston, IL (US); Russell D. Cink, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/886,318

(22) Filed: Feb. 1, 2018

(65) Prior Publication Data
US 2018/0258451 A1   Sep. 13, 2018

Related U.S. Application Data

(60) Provisional application No. 62/453,246, filed on Feb. 1, 2017.

(51) Int. Cl.
| | | |
|---|---|---|
| *C12P 7/62* | (2006.01) | |
| *C12P 7/40* | (2006.01) | |
| *C12N 9/18* | (2006.01) | |
| *C07C 67/343* | (2006.01) | |

(52) U.S. Cl.
CPC .............. *C12P 7/62* (2013.01); *C07C 67/343* (2013.01); *C12N 9/18* (2013.01); *C12Y 301/01001* (2013.01); *C12Y 304/21014* (2013.01)

(58) Field of Classification Search
CPC .............. C12P 7/62; C12Y 304/21014; C12Y 301/01001; C12N 9/18
USPC ............... 435/135, 195, 136, 142, 197, 221; 514/784
See application file for complete search history.

(56) References Cited

U.S. PATENT DOCUMENTS

| | | |
|---|---|---|
| 4,952,496 A | 8/1990 | Studier et al. |
| 5,693,489 A | 12/1997 | Studier et al. |
| 5,869,320 A | 2/1999 | Studier et al. |
| 9,809,534 B1 | 11/2017 | Lukin et al. |
| 9,809,576 B1 | 11/2017 | Cink et al. |
| 1,005,996 A1 | 8/2018 | Abrahamson et al. |
| 1,011,315 A1 | 10/2018 | Abrahamson et al. |
| 10,316,338 B1 | 6/2019 | Abrahamson et al. |
| 10,465,216 B2 | 11/2019 | Abrahamson et al. |
| 2011/0212504 A1 | 9/2011 | Liu |
| 2011/0229940 A1 | 9/2011 | Nojiri et al. |
| 2012/0070416 A1 | 3/2012 | Or et al. |
| 2013/0096339 A1 | 4/2013 | Asuma et al. |
| 2015/0175626 A1 | 6/2015 | Cagulada et al. |
| 2016/0361375 A1 | 12/2016 | Bjornson et al. |
| 2018/0057482 A1 | 3/2018 | Cink et al. |
| 2018/0194721 A1 | 7/2018 | Lukin et al. |
| 2018/0258451 A1 | 9/2018 | Abrahamson et al. |

FOREIGN PATENT DOCUMENTS

| | | |
|---|---|---|
| WO | WO-2008/067981 A2 | 6/2008 |
| WO | WO-2010/030359 A2 | 3/2010 |
| WO | WO-2010/050516 A1 | 5/2010 |
| WO | WO-2018/144681 A1 | 8/2018 |

OTHER PUBLICATIONS

Whisstock et al., (Quarterly Reviews of Biophysics 2003, vol. 36 (3): 307-340.*
Kisselev L., (Structure, 2002, vol. 10: 8-9.*
Witkowski et al., (Biochemistry 38:11643-11650, 1999.*
Devos et al., (Proteins: Structure, Function and Genetics, 2000, vol. 41: 98-107.*
U.S. Appl. No. 14/873,706, AbbVie Inc.
U.S. Appl. No. 14/874,001, Abrahamson et al.
U.S. Appl. No. 15/010,557, Abrahamson et al.
Nobili et al., "Use of 'Small but Smart' Libraries to Enhance the Enantioselectivity of an Esterase for Bacillus Stearothermophilus Towards Tetrahydrofuran-3-yl Acetate," FEBS Journal, 280(12):3084-3091 (2013).
International Search Report and Written Opinion for International Application No. PCT/US18/16362 dated Jul. 6, 2018.
Branden et al., "Prediction, Engineering, and Design of Protein Structures," Introduction to Protein Structure, pp. 247 (1991).
Faucher, A.M. et al., "Synthesis of BILN 2061, an HCV NS3 Protease Inhibitor with Proven Antiviral Effect in Humans," Org Lett, 6(17):2901-04 (2004).
Kaneko et al., Q8YZN1—UniProtKB Database, May 3, 2013.
Nierman, "Complete genome sequence of Caulobacter crescentus," UniProtKB database No. Q9A6L1, 2013.
Park et al., "Asymmetric Syntheses of iso-Boc (S)-2-Amino-8-nonenoic Acid in One Through-Process," Org Process Res Dev, 20:76-80 (2016).
Wang, X.J. et al., "Efficient Synthesis of (S)-2-(Cyclopentyloxycarbonyl)-amino-8-nonenoic Acid: Key Building Block for BILN 2061, an HCV NS3 Protease Inhibitor," Org Process Res Dev, 11:60-3 (2007).
Studer et al., "Residue mutations and their impact on protein structure and function: detecting beneficial and pathogenic changes," Biochem J, 449(3):581-594 (2013).

* cited by examiner

*Primary Examiner* — Robert B Mondesi
*Assistant Examiner* — Mohammad Y Meah
(74) *Attorney, Agent, or Firm* — Foley Hoag LLP (57) ABSTRACT

Disclosed are methods of synthesizing racemic 2-(difluoromethyl)-1-(alkoxycarbonyl)-cyclopropanecarboxylic acids and 2-(vinyl)-1-(alkoxycarbonyl)-cyclopropanecarboxylic acids and their salts, such as the dicyclohexylamine salt. Also disclosed are methods for preparing enantioenriched (1R,2R)-1-((tert-butoxycarbonyl)amino)-2-(difluoromethyl)cyclopropane-1-carboxylic acid and esters of the same. These compounds are useful intermediates in the synthesis of viral protease inhibitors.

11 Claims, 3 Drawing Sheets

Specification includes a Sequence Listing.

ENZYMATIC PROCESSES FOR THE PREPARATION OF (±)-2-(DIFLUOROMETHYL)-1-(ALKOXYCARBONYL)-CYCLOPROPANECARBOXYLIC ACID AND (±)-2-(VINYL)-1-(ALKOXYCARBONYL)-CYCLOPROPANECARBOXYLIC ACID

RELATED APPLICATIONS

This application claims the benefit of priority to U.S. Provisional Patent Application Ser. No. 62/453,246, filed Feb. 1, 2017.

SEQUENCE LISTING

The instant application contains a Sequence Listing which has been submitted electronically in ASCII format and is hereby incorporated by reference in its entirety. Said ASCII copy, created on Nov. 11, 2019, is named AVR 05201 SL.txt and is 9,314 bytes in size.

BACKGROUND

Complex biologically active molecules are challenging, expensive, and time-consuming to synthesize. Synthesizing compounds with good levels of diastereoselectivity is even more challenging. Doing so generally involves isolating or synthesizing a diasterioenriched intermediate the stereochemistry of which can be preserved in the required subsequent synthetic transformations.

An example of a useful intermediate in the synthesis of a biologically active molecule is (±)-2-(difluoromethyl)-1-(ethoxycarbonyl)cyclopropanecarboxylic acid. In the past, this intermediate was synthesized as shown in Scheme 1, from diethyl 0-2-(difluoromethyl)cyclopropane-1,1-dicarboxylate using a hydrolysis method that yielded modest diastereoselectivity:

There exists a need for new synthetic methods to construct enantioenriched difluoroalkylcyclopropyl and vinylalkylcyclopropyl esters in higher levels of diastereoselectivity.

SUMMARY OF THE INVENTION

In certain embodiments, the invention relates to a method according to reaction Scheme A:

wherein $R^1$ is $(C_1-C_6)$alkyl;
$R^2$ is $-CF_2H$ or $-CH=CH_2$; and
the first enzyme is a mutant of BsteE esterase.
In further embodiments, the invention relates to a method according to reaction Scheme B:

wherein $R^1$ is $(C_1-C_6)$alkyl;
$R^2$ is $-CF_2H$; and
the second enzyme is selected from the group consisting of Alcalase® 2.4 L, Esperase® 8.0 L, and Savinase® 16.0 L.

The invention further provides polypeptides, comprising an amino acid sequence having at least two amino acid substitutions relative to SEQ ID NO: 2, wherein the amino acid sequence comprises a first mutation of T25H, and a second mutation of L92H.

DETAILED DESCRIPTION OF THE INVENTION

I. Overview

Figure 1:
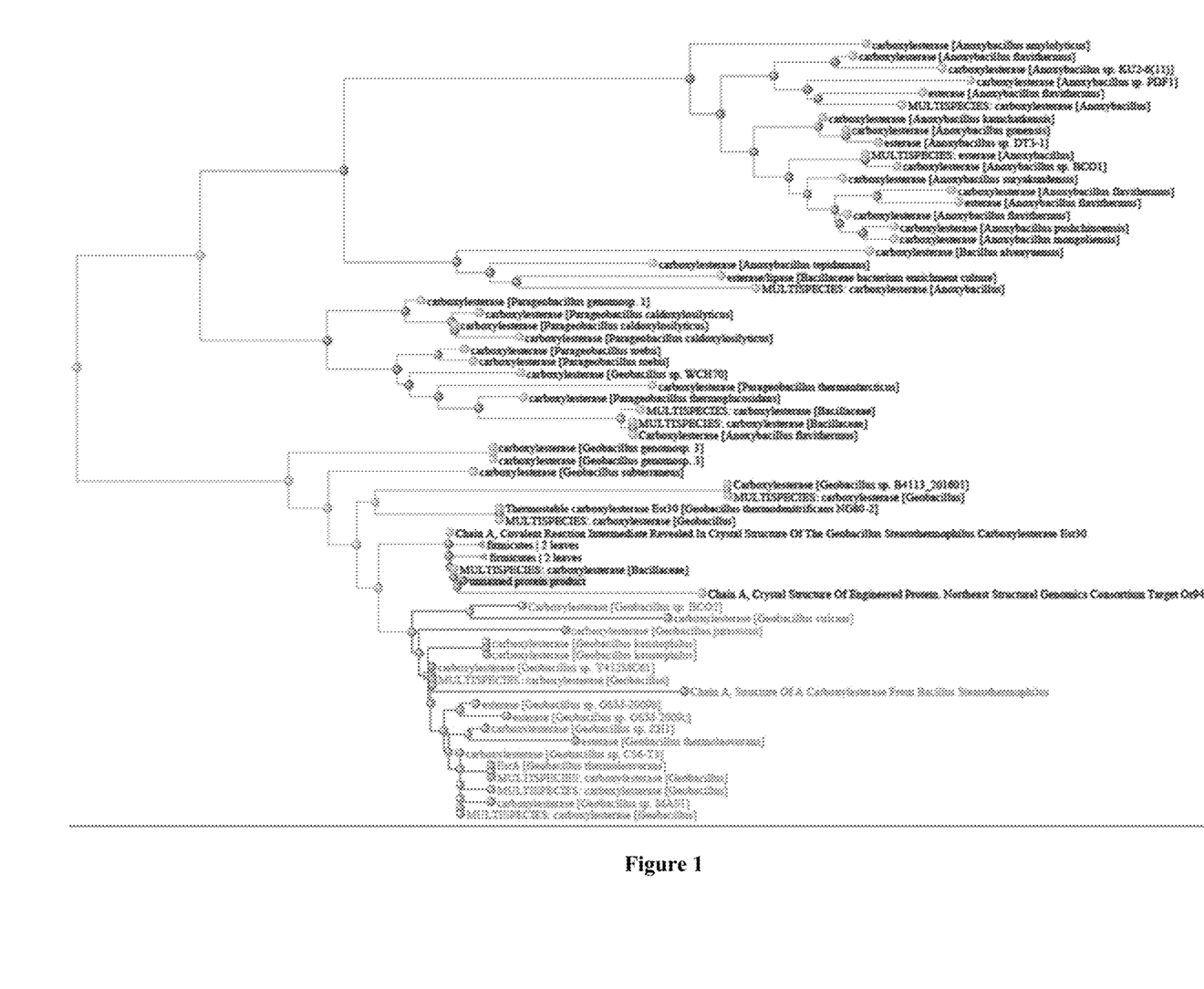
FIG. 1 is the family tree for BsteE esterase. Enzymes closely related to BsteE esterase have similar amino acid sequences, and thus can function similarly to BsteE esterase in the diastereoselective methods described herein.
Figure 2:
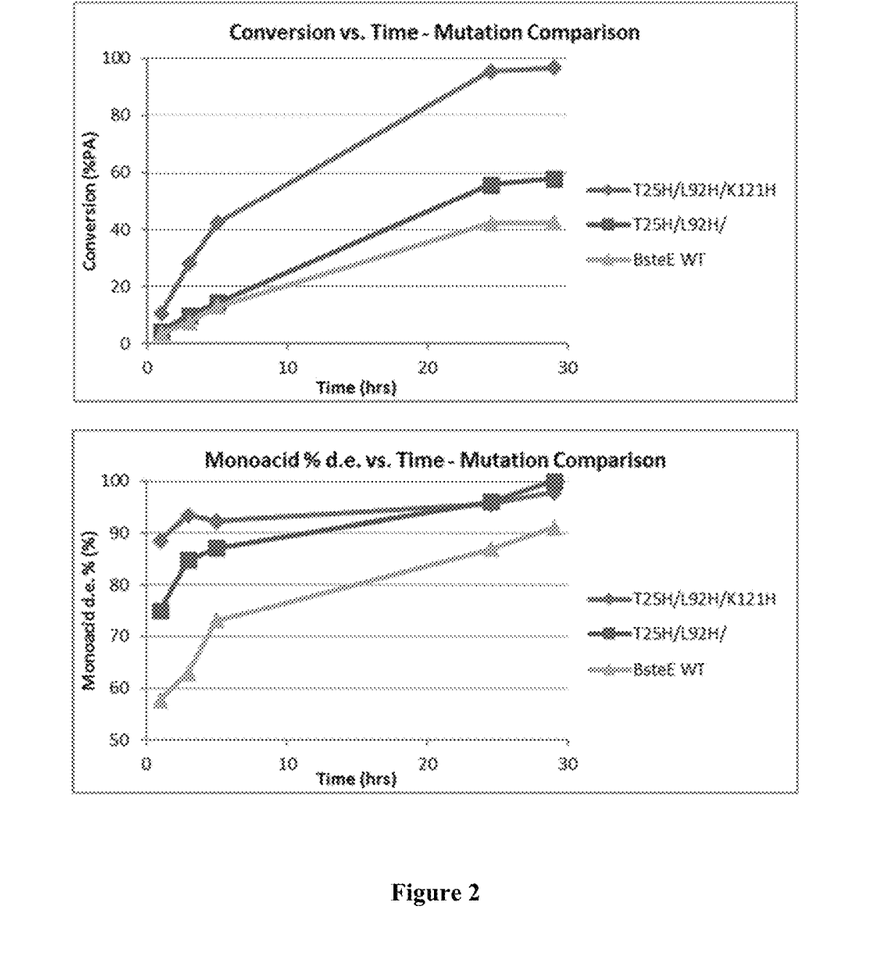
FIG. 2 contains two charts showing a comparison of conversion and diastereomeric selectivity (% d.e.) of mutants T25H/L92H and T25H/L92H/K121H versus *B. stearothermophilus* wild-type esterase. Reaction conditions: 200 mM NaHPO₄ pH 8, 250 RPM, 40° C., 10 g/L substrate, 10 mL reaction volume, and 1 mg/mL clarified lysate of each enzyme.
Figure 3:
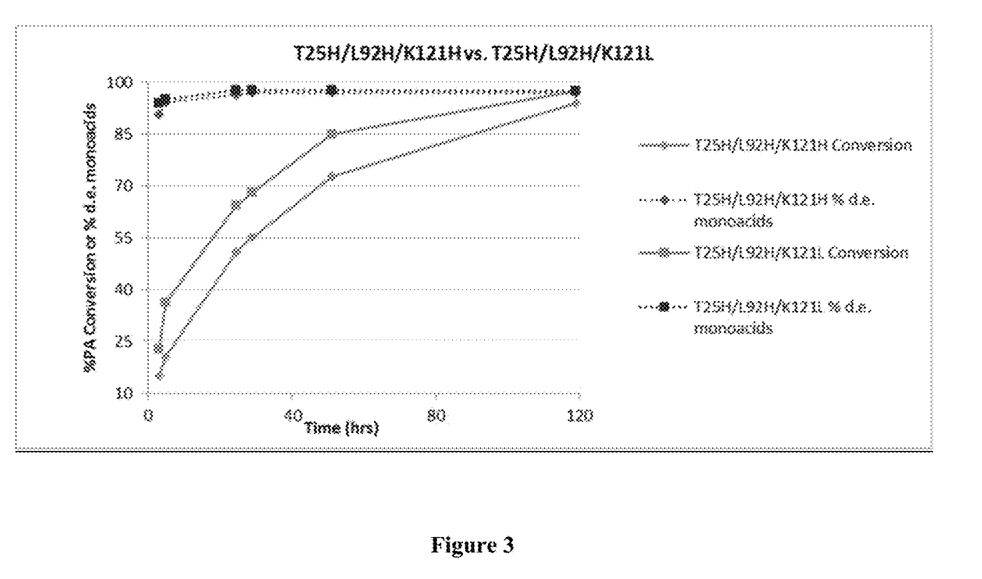
FIG. 3 is a chart showing a comparison of conversion and diastereomeric selectivity (% d.e.) of mutants T25H/L92H and T25H/L92H/K121H versus *B. stearothermophilus* wild-type esterase. Reaction conditions: 200 mM NaHPO₄ pH 8, 250 RPM, 40° C., 10 g/L substrate, 10 mL reaction volume, and 1 mg/mL clarified lysate of each enzyme.

In certain embodiments, the invention relates to a method of synthesizing diastereoenriched compounds, such as ((±)-2-(difluoromethyl)-1-(ethoxycarbonyl)cyclopropanecarboxylic acid, by diastereoselective enzymatic hydrolysis. The inventive methods are more efficient than known methods because (i) they do not involve synthesizing a racemate and separating diastereomers, and (ii) they yield compounds with high levels of diastereomeric enrichment. The invention described herein also relates to active and diastereoselective mutant enzymes that achieve this transformation. The mutant enzymes of the invention exhibit improved properties over the wild-type enzyme, including, increased activity toward the desired substrate, suppressed production of undesired diastereomers, and roughly equivalent activity to the individual isomers of the desired enantiomer pair, yielding a diastereoenriched racemate.

The diastereoselective enzymatic hydrolysis described herein provides an advantage over known methods by improving product yield and diastereoselectivity while eliminating the need for certain processing steps. For example, the methods described herein eliminate two MTBE slurrying steps utilized in known methods. The improved methods presented herein enable, e.g., higher throughput for the chemical synthesis.

In certain embodiments, the invention relates to a method of synthesizing a Drug Substance via (1R,2R)-1-((tert-butoxycarbonyl)amino)-2-(difluoromethyl) cyclopropanecarboxylic acid as shown in Scheme 2. In certain embodiments, a Drug Substance may alternatively be synthesized via the intermediacy of ((±)-2-(vinyl)-1-(ethoxycarbonyl)cyclopropanecarboxylic acid.

Scheme 2: Structure of (±)-2-(difluoromethyl)-1-(ethoxycarbonyl) cyclopropane carboxylic acid, and its conversion to Drug Substance In certain embodiments, the racemic diester starting material is produced according to the method of Scheme 3. The diastereoselective enzymatic hydrolysis described herein transforms the diester starting material into a desired product, diastereoenriched (±)-2-(difluoromethyl)-1-(alkoxycarbonyl)cyclopropanecarboxylic acid, as demonstrated in Scheme 4.

In certain embodiments, the methods improve processability of the isolated intermediates.

In certain embodiments, the methods described herein improve the diastereoselectivity of the hydrolysis reaction.

In certain embodiments, the methods described herein improve the product yield of the hydrolysis reaction.

II. Definitions

Listed below are definitions of various terms used to describe this invention. These definitions apply to the terms as they are used throughout this specification and claims, unless otherwise limited in specific instances, either individually or as part of a larger group.

The number of carbon atoms in a hydrocarbyl substituent can be indicated by the prefix "$C_x$-$C_y$," where x is the minimum and y is the maximum number of carbon atoms in the substituent. "($C_x$)alkyl" indicates an alkyl group composed of x number of carbon atoms.

The term "alkyl" as used herein, refers to a saturated, straight- or branched-chain hydrocarbon radical typically containing from 1 to 20 carbon atoms. For example, "$C_1$-$C_6$ alkyl" or "$C_1$-$C_8$ alkyl" contains from one to six, or from one to eight, carbon atoms, respectively. Examples of alkyl substituents include, but are not limited to, methyl, ethyl, propyl, isopropyl, n-butyl, tert-butyl, neopentyl, n-hexyl, heptyl, octyl substituents and the like.

As used herein, the term "salt" includes "pharmaceutically acceptable salts," which are, within the scope of sound medical judgment, suitable for use in contact with the tissues of humans and other vertebrates, preferably mammals, without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977). Such salts can be prepared in situ during isolation and purification of reaction products as described herein, or separately, such as by reacting a free base function with a suitable acid, such as an organic acid. Examples of pharmaceutically acceptable salts include, but are not limited to, hydrochloride, hydrobromide, phosphate, sulfate, perchlorate, acetate, maleate, tartrate, citrate, succinate, or malonate. Other pharmaceutically acceptable salts include, but are not limited to, adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, sulfate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, ammonium, quaternary ammonium, and amine cations associated with counterions such as halide, hydroxide, carboxylate, sulfate, phosphate, nitrate, alkyl having from 1 to 6 carbon atoms, sulfonate and aryl sulfonate.

As used herein, the term "enantioenriched" means a mixture of enantiomers in which one of the two enantiomers is present in a larger amount (e.g., having an enantiomeric excess (ee) greater than about 90%, greater than about 95%, preferably greater than about 98%, most preferably greater than 99%). This term also encompasses an enantiomerically pure compound.

As used herein, the term "diastereoenriched" means a mixture of diastereomers in which one of the diastereomers is present in a larger amount (e.g., having an diastereomeric excess (de) greater than about 90%, greater than about 95%, preferably greater than about 98%, most preferably greater than 99%). This term also encompasses an diastereomerically pure compound.

Various aspects of the invention are described in further detail herein.

III. Exemplary Methods and Uses

The compounds and processes of the present invention will be better understood in connection with the following illustrative methods, by which the compounds of the invention may be prepared. It will be understood that any reaction described herein, in any of its variations, can be combined in sequence with one or more of the other reactions described herein, in any of their variations, substantially in analogy with the sequence shown in the Schemes.

In certain embodiments, the invention relates to a method comprising a reactive resolution according to reaction Scheme A:

Scheme A wherein $R^1$ is ($C_1$-$C_6$)alkyl;
$R^2$ is —$CF_2H$ or —CH=$CH_2$; and
the first enzyme is a mutant of BsteE esterase.

In certain embodiments, $R^1$ is ($C_6$)alkyl. Alternatively, $R^1$ can be ($C_5$)alkyl, ($C_4$)alkyl, ($C_3$)alkyl (such as n-propyl or isopropyl), ethyl, or methyl. In certain embodiments, $R^1$ is ethyl.

In certain embodiments, $R^2$ is —$CF_2H$. In alternative embodiments, $R^2$ is —CH=$CH_2$.

In certain embodiments, the mutant of BsteE esterase comprises a first mutation of T25H, a second mutation of L92H, and a third mutation selected from the group consisting of K121R, K121Y, K121H, K121D, K121L, M126F, M126V, M126I, M126Q, M194L, M194A, L166N, L166M, I170N, and I170Q.

In certain such embodiments, the third mutation is selected from the group consisting of K121R, K121Y, K121H, K121D, K121L, M126V, M126I, M126Q, M194L, and L166M. In further such embodiments, the third mutation is selected from the group consisting of K121Y, K121H, K121D, K121L, M126V, M126I, M126Q, and L166M. In certain embodiments, the third mutation is selected from the group consisting of K121Y, K121H, K121D, and K121L.

In certain embodiments, the loading of the first enzyme is from about 50 wt % to about 200 wt % as compared to the starting material, for example, about 50 wt %, about 60 wt %, about 70 wt %, about 80 wt %, about 90 wt %, about 100 wt %, about 110 wt %, about 120 wt %, about 130 wt %, about 140 wt %, about 150 wt %, about 160 wt %, about 170 wt %, about 180 wt %, about 190 wt %, or about 200 wt %, preferably about 100 wt % as compared to starting material.

In certain embodiments, the first solvent comprises one or more organic solvents. For example, the solvent may comprise heptane and methyl tert-butyl ether.

In certain embodiments, the first solvent further comprises an aqueous buffer.

In certain embodiments, the aqueous buffer is an aqueous solution of sodium citrate or calcium acetate, e.g., at a concentration of from about 0.05 M to about 2.0 M, for example, about 0.05 M, about 0.06 M, about 0.07 M, about 0.08 M, about 0.09 M, about 0.10 M, about 0.11 M, about 0.12 M, about 0.13 M, about 0.14 M, about 0.15 M, about 0.2 M, about 0.3 M, about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, or about 2.0 M. In certain embodiments, the concentration is about 0.1 M.

In certain embodiments, the first solvent further comprises a base. In certain embodiments, the base is a di(alkyl)

amine, such as a di(cycloalkyl)amine or a di(aralkyl)amine. In certain embodiments, the base is di(cyclohexyl)amine or di(benzyl)amine.

In certain embodiments, the first pH is about 5 to about 10, for example, about 5, about 5.25, about 5.5, about 5.75, about 6, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, or about 10.0. In certain embodiments, the first pH is about 5 to about 6.5. In certain embodiments, the first pH is about 5.75.

In certain embodiments, the first temperature is about 10° C. to about 60° C., for example, about 15° C., about 20° C., about 25° C., about 30° C., about 35° C., about 40° C., about 45° C., about 50° C., about 55° C., or about 60° C. In certain embodiments, the first temperature is about 20° C.

In certain embodiments, the first period of time is about 2 h to about 8 h, for example, about 2 h, about 4 h, about 6 h, about 8 h. Alternatively, the first period of time is from about 2 h to about 48 h, for example, about 2 h, about 4 h, about 6 h, about 8 h, about 10 h, about 12 h, about 14 h, about 16 h, about 18 h, about 20 h, about 22 h, about 24 h, about 26 h, about 28 h, about 30 h, about 32 h, about 34 h, about 36 h, about 38 h, about 40 h, about 42 h, about 44 h, about 46 h, or about 48 h.

In certain embodiments, the method further comprises contacting the reaction product of reaction Scheme A with a base to obtain a salt of the compound.

In certain such embodiments, the base is a di(alkyl)amine, such as a di(cycloalkyl)amine or a di(aralkyl)amine. Preferably, the base is di(cyclohexyl)amine or di(benzyl)amine.

In certain embodiments, the diastereomeric excess of the reaction product is greater than about 90%. In further embodiments, the diastereomeric excess of the reaction product is greater than about 95%.

In certain embodiments, the invention relates to a method comprising a reactive resolution according to reaction Scheme B:

Scheme B wherein $R^1$ is $(C_1-C_6)$alkyl;

$R^2$ is $-CF_2H$ or $-CH=CH_2$, preferably $-CF_2H$; and the second enzyme is selected from the group consisting of Alcalase® 2.4 L, Esperase® 8.0 L, and Savinase® 16.0 L.

Alcalase® 2.4 L, Esperase® 8.0 L, and Savinase® 16.0 L are each available from Novozymes. In certain embodiments of the reaction depicted in Scheme B, the second enzyme is Alcalase® 2.4 L.

Alcalase® is type of subtilisin, a protease from *Bacillus licheniformis*. Alcalase® acts as an esterase, enabling it to catalyze stereoselective hydrolysis of some esters and to catalyze hydrolysis of amino esters, including heterocyclic amino esters.

Savinase® is a protease from *Bacillus* sp., and is a serine endopeptodase. It can catalyze stereoselective hydrolysis of some esters as well as strained amides under alkaline conditions.

Esperase® is an endopeptidase (mainly subtilisin A) with a broad specificity, which performs well under alkaline conditions and at elevated temperatures, as compared to other microbial serine proteases. Applications include the hydrolysis of internal peptide bonds. Esperase® is characterized by excellent performance at elevated temperatures and pH.

In certain embodiments, the loading of the second enzyme is about 50 wt % to about 200 wt % as compared to the starting material in Scheme B, for example, about 50 wt %, about 60 wt %, about 70 wt %, about 80 wt %, about 90 wt %, about 100 wt %, about 110 wt %, about 120 wt %, about 130 wt %, about 140 wt %, about 150 wt %, about 160 wt %, about 170 wt %, about 180 wt %, about 190 wt %, or about 200 wt %, preferably about 120 wt % to about 140 wt %, or about 130 wt %, as compared to starting material in Scheme B.

In certain embodiments, the second solvent comprises an aqueous buffer. In certain embodiments, the aqueous buffer is an aqueous solution of sodium bicarbonate and/or sodium carbonate, e.g., at a concentration of from about 0.05 M to about 2.0 M, for example, about 0.05 M, about 0.06 M, about 0.07 M, about 0.08 M, about 0.09 M, about 0.10 M, about 0.11 M, about 0.12 M, about 0.13 M, about 0.14 M, about 0.15 M, about 0.2 M, about 0.3 M, about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, or about 2.0 M. In certain embodiments, the concentration is about 0.1 M.

In certain embodiments, the second solvent further comprises an organic solvent. Exemplary organic solvents that may be used in the methods of the invention include acetone, acetonitrile, dimethylformamide, dioxane, ethanol, isopropanol, and dimethylsulfoxide. In some preferred embodiments, the organic solvent used in the reaction method of Scheme B is acetone. In certain embodiments, the organic solvent is approximately 5% to approximately 75% of the total volume of the second solvent. For example, the organic solvent may be about 5%, 10%, 15%, 20%, 25%, 30%, 35%, 40%, 45%, 50%, 55%, 60%, 65%, or 70% volume relative to total volume of the second solvent. In some embodiments, the organic solvent is approximately 5%-20% of the total volume of the second solvent, preferably 10%.

In certain embodiments, the second pH is about 5 to about 10, for example, about 5, about 5.25, about 5.5, about 5.75, about 6, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, or about 10.0. In certain embodiments, the second pH is about 7.5 to about 9. In certain embodiments, the first pH is about 8.0.

In certain embodiments, the second temperature is about 10° C. to about 60° C., for example, about 15° C., about 20° C., about 25° C., about 30° C., about 35° C., about 40° C., about 45° C., about 50° C., about 55° C., or about 60° C. In certain embodiments, the second temperature is about 40° C.

In certain embodiments, the second period of time is about 2 h to about 8 h, for example, about 2 h, about 4 h, about 6 h, about 8 h. Alternatively, the second period of time is from about 2 h to about 48 h, for example, about 2 h, about 4 h, about 6 h, about 8 h, about 10 h, about 12 h, about 14 h, about 16 h, about 18 h, about 20 h, about 22 h, about 24 h, about 26 h, about 28 h, about 30 h, about 32 h, about 34 h, about 36 h, about 38 h, about 40 h, about 42 h, about 44 h, about 46 h, or about 48 h.

In certain embodiments, the invention relates to methods comprising two or more of the steps described herein. For example, the invention may relate to methods comprising the methods of Scheme A and Scheme B.

In certain embodiments, the invention relates to the use of any of the compounds described herein in the manufacture of a medicament.

Definitions of variables in the structures in the schemes herein are commensurate with those of corresponding positions in the formulae delineated herein.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers. Racemates, and Resolutions (John Wiley & Sons, 1981).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 2d. Ed., John Wiley and Sons (1991): L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

IV. Polypeptides

In certain embodiments, the invention provides polypeptides that are mutants of BsteE esterase and enzymatically active fragments thereof. In some embodiments, the polypeptide is a variant of BsteE esterase, or an enzymatically active fragments thereof. An exemplary DNA sequence for the full-length, wild-type *Bacillus stearothermophilus* (BsteE) esterase is as follows:

```
                                            (SEQ ID NO: 1)
ATGGCGAAGATTGTCCCGCCGAAGCCGTTTTTCTTTGAAGCCGGTGAACG

TGCTGTCCTGCTGCTGCATGGTTTTACCGGTAACTCCGCTGATGTGCGTA

TGCTGGGCCGCTTTCTGGAATCCAAAGGTTATACCTGCCATGCGCCGATT

TACAAGGGCCACGGTGTCCCGCCGGAAGAACTGGTGCATACGGGTCCGGA

TGACTGGTGGCAGGATGTTATGAACGGCTACGAATTTCTGAAGAACAAGG

GTTACGAAAAGATCGCAGTGGCAGGTCTGAGCCTGGGCGGTGTTTTCAGC

CTGAAACTGGGCTATACCGTTCCGATTGAAGGTATCGTCACGATGTGTGC

ACCGATGTATATTAAAAGCGAAGAAACCATGTACGAAGGTGTGCTGGAAT

ATGCTCGTGAATACAAAAAGCGCGAAGGCAAATCTGAAGAACAGATCGAA

CAAGAAATGGAAAAGTTCAAGCAGACCCCGATGAAAACGCTGAAGGCACT

GCAAGAACTGATTGCTGATGTTCGTGACCATCTGGATCTGATCTATGCAC

CGACCTTCGTGGTTCAGGCACGTCACGACGAAATGATTAACCCGGATTCA

GCGAACATCATCTACAACGAAATCGAATCGCCGGTCAAACAGATCAAGTG

GTACGAACAAAGCGGTCACGTGATTACGCTGGACCAGGAAAAAGATCAAC

TGCATGAAGACATCTACGCCTTCCTGGAAAGTCTGGATTGGTGACTCGAG.
```

Translation of the DNA sequence of wild-type *Bacillus stearothermophilus* (BsteE) esterase yields a polypeptide having the sequence of SEQ ID NO:2:

```
                                            (SEQ ID NO: 2)
MAKIVPPKPFFFEAGERAVLLLHGFTGNSADVRMLGRFLESKGYTCHAPI

YKGHGVPPEELVHTGPDDWWQDVMNGYEFLKNKGYEKIAVAGLSLGGVFS

LKLGYTVPIEGIVTMCAPMYIKSEETMYEGVLEYAREYKKREGKSEEQIE

QEMEKFKQTPMKTLKALQELIADVRDHLDLIYAPTFVVQARHDEMINPDS

ANIIYNEIESPVKQIKWYEQSGHVITLDQEKDQLHEDIYAFLESLDW.
```

The polypeptide sequence of wild-type *Bacillus stearothermophilus* (BsteE) esterase, minus the methionine residue encoded by the start codon ATG, is represented by SEQ ID NO:10:

```
                                            (SEQ ID NO: 10)
AKIVPPKPEFFEAGERAVLLLHGFTGNSADVRMLGRFLESKGYTCHAPIY

KGHGVPPEELVHTGPDDWWQDVNINGYEFLKNKGYEKIAVAGLSLGGVFS

LKLGYTVPIEGIVTMCAPMYIKSEETMYEGVLEYAREYKKREGKSEEQIE

QEMEKFKQTPMKTLKALQELIADVRDHLDLIYAPTFVVQARHDEMINPDS

ANIIYNEIESPVKQIKWYEQSGHVITLDQEKDQLHEDIYAFLESLDW
```

Accordingly, in certain embodiments, the amino acid sequence of the mutant of BsteE esterase used in the methods of the invention has at least 50% homology, at least 55% homology, at least 60% homology, at least 65% homology, at least 70% homology, at least 75% homology, at least 80% homology, at least 82% homology, at least 84% homology, at least 86% homology, at least 88% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 2.

In other embodiments, the invention provides a polypeptide, comprising
an amino acid sequence having at least two amino acid substitutions relative to SEQ ID NO: 2, wherein the amino acid sequence comprises a first mutation of T25H and a second mutation of L92H.

In still yet other embodiments, the invention provides a polypeptide, comprising
an amino acid sequence having at least 95% homology to SEQ ID NO: 2 and having at least two amino acid substitutions relative to SEQ ID NO: 2, wherein the amino acid sequence comprises a first mutation of T25H and a second mutation of L92H.

In certain such embodiments, the polypeptide comprises a third amino acid substitution selected from the group consisting of K121R, K121Y, K121H, K121D, K121L, M126F, M126V, M126I, M126Q, M194L, M194A, L166N, L166M, I170N, and I170Q.

In certain such embodiments, the third amino acid substitution is selected from the group consisting of K121R, K121Y, K121H, K121D, K121L, M126V, M126I, M126Q, M194L, and L166M.

In further embodiments, the third amino acid substitution is selected from the group consisting of K121Y, K121H, K121D, K121L, M126V, M126I, M126Q, and L166M.

In yet further embodiments, the third amino acid substitution is selected from the group consisting of K121Y, K121H, K121D, and K121L.

In certain embodiments, the DNA sequence of wild-type *Bacillus stearothermophilus* (BsteE) esterase has the sequence of SEQ ID NO: 3:

```
                                            (SEQ ID NO: 3)
ATGGGCAAAATCGTCCCGCCGAAACCGTTCTTCTTTGAAGCTGGTGAACG

TGCTGTGCTGCTGCTGCATGGCTTTCATGGCAATAGCGCCGACGTTCGTA

TGCTGGGCCGCTTTCTGGAAAGCAAAGGTTATACCTGCCATGCACCGATT

TACAAAGGCCACGGTGTCCCGCCGGAAGAACTGGTGCATACGGGTCCGGA

TGACTGGTGGCAGGATGTCATGAACGGCTACGAATTTCTGAAAAACAAAG

GTTACGAAAAAATCGCAGTGGCAGGTCATAGCCTGGGTGGTGTTTTCTCT

CTGAAACTGGGCTATACCGTTCCGATTGAAGGTATCGTCACGATGTGTGC

ACCGATGTACATCTTATCAGAAGAAACCATGTACGAAGGTGTGCTGGAAT

ATGCTCGTGAATACAAAAAACGCGAAGGCAAATCGGAAGAACAGATCGAA

CAAGAAATGGAAAAATTCAAACAGACCCCGATGAAAACGCTGAAAGCACT

GCAAGAACTGATTGCTGATGTTCGTGACCATCTGGATCTGATCTATGCAC

CGACCTTCGTGGTTCAGGCACGTCACGACGAAATGATTAACCCGGATAGT

GCCAACATCATCTACAACGAAATCGAATCCCCGGTCAAACAGATCAAATG

GTACGAACAAAGTGGCCACGTGATCACGCTGGATCAGGAAAAAGACCAAC

TGCACGAAGACATTTACGCATTTCTGGAATCGCTGGACTGGTAA.
```

Translation of the DNA sequence of SEQ ID NO: 3 yields a polypeptide having the sequence of SEQ ID NO:4. T25H, L92H, and K121L mutations are indicated in bold, underline font:

```
                                             (SEQ ID NO: 4)
MGKIVPPKPFFFEAGERAVLLLHGFHGNSADVRMLGRFLESKGYTCHAPI

YKGHGVPPEELVHTGPDDWWQDVMNGYEFLKNKGYEKIAVAGHSLGGVFS
```

LKLGYTVPIEGIVTMCAPMYILSEETMYEGVLEYAREYKKREGKSEEQIE

QEMEKFKQTPMKTLKALQELIADVRDHLDLIYAPTFVVQARHDEMINPDS

ANIIYNEIESPVKQIKWYEQSGHVITLDQEKDQLHEDIYAFLESLDW.

In certain embodiments, the mutant of BsteE esterase used in the methods of the invention comprises a set of mutations selected from the group consisting of:

T25H/L92H/K121L; T25H/L92H/K121H; T25H/L92H/K121H/I195L; T25H/L92H; T25H/L92H/K215N; T25H/L92H/D172N; T25H/L92H/M126Q; T25H/L92H/E123T; T25H/L92H/M126V; T25H/L92H/M126I; T25H/L92H/K121Y; T25H/L92H/M194A; T25H/L92H/K121H; T25H/L92H/L166M; T25H/L92H/K121R; T25H/L92H/K164S; T25H/L92H/M126F; T25H/L92H/M194L; T25H/L92H/L166N; T25H/L92H/I170N; T25H/L92H/I170Q; T25H/L92H/I170N; T25H/L92H/K121H/I170N; T25H/L92H/K121H/K164S; T25H/L92H/K121H/L166M; T25H/L92H/K121H/I170N; T25H/L92H/K121H/I195G; T25H/L92H/K121H/I195A; T25H/L92H/K121H/I195V; T25H/L92H/K121H/C115S; T25H/L92H/K121H/C115A; T25H/L92H/K121H/I170V; T25H/L92H/K121H/L166I; 25H/L92H/I170T; T25H/L92H/I170A; T25H/L92H/M126N; T25H/L92H/L166T; T25H/L92H/L166A; T25H/L92H/K121H/I170N; T25H/L92H/K121H/I170V; T25H/L92H/K121D; T25H/L92H/K121T; T25H/L92H/K121A; and T25H/L92H/K121N.

In further embodiments, the mutant of BsteE esterase used in the methods of the invention comprises a set of mutations selected from the group consisting of:

T25F/L92H; T25F/L92H/I170Q; T25F/I170Q; L166H; T25F; T25H; T25F/K121Y/L166M; T25H/K121H; I170N; L166M; F24C/T25F; T25N; and I92H.

In further embodiments, the mutant of BsteE esterase used in the methods of the invention comprises one or more of the following mutations:

| Wild Type Residue | Mutant Residue |
| --- | --- |
| T25 | H, A, I, R, K, F, N, V, L |
| L92 | H, K, R, A, I, V, L |
| K121 | H, R, L, I, V, A, K, Y, N |
| L166 | I, M, A, V, G, L, N, F |
| L195 | L, G, A, V, I, N, Q |
| F24 | C, N, Q, G, I, A, V, L |
| M126 | F, Q, N, A, I, V, L |
| I170 | Q, N, A, I, V, L |
| M194 | A, I, V, L, G. |

EXEMPLIFICATION

The present invention is further illustrated by the following Example which should not be construed as limiting in any way. The Examples and discoveries described herein are representative. As such, the studies and results described in the Examples section herein may be used as a guideline.

Example 1: Diastereoselective Enzymatic Hydrolysis

Example 1a: Screen for Enzymes Capable of Diastereoselective Enzymatic Hydrolysis Enzyme variants were compared against the wild-type enzyme and other enzyme variants using a lab-scale hydrolysis reaction under identical conditions and uniform sampling procedure. The uniformity of reaction conditions and sample timing allowed for relative comparison of rates and selectivity at each time point (i.e., 4 hrs) across variants. Each mutant was expressed using traditional competent E. coli fermentation conditions (25° C., 250 RPM, 50 mL Invotrogen MagicMedia # K6803, 1% inoculum from an overnight culture, expressed for 24 hours). Cell cultures were harvested by centrifugation of the total 50 mL volume, followed by resuspension of the cell pellet in 5 mL 200 mM NaHPO$_4$ buffer, pH 8. The cell suspension was sonicated (3×30 s) to lyse cells and centrifuged to pellet cell debris (35 min at 6000 RPM). The resulting 5 mL of clarified lysate was used as the active enzyme solution in the screening reactions.

Reactions were prepared in a 20 mL vial by combining 5 mL of 200 mM NaHPO$_4$ buffer, pH 8 and 100 μL of (±)-dipropyl 2-(difluoromethyl)cyclopropane-1,1-carboxylate (final concentration of approximate 10 g diester/L). The 5 mL of clarified lysate was added to each reaction (t=0 hr), and the reaction incubated at 40° C. with 250 RPM agitation with a diamond-shaped magnetic stir bar. Reaction aliquots of 500 μL were taken at 2, 4, and 18 hours for analysis. Aliquots were combined with 3 drops of 20% HCl solution and extracted into 1 mL MTBE. The organic phase was analyzed by chiral normal phase HPLC to determine conversion and selectivity. (Column: Phenomenex Lux 3 μm Cellulose-2; 250 mm×4.6 mm; 20° C.; Mobile phase: Heptane/iPrOH/TFAA, 98.5/1.5/0.1; Flow: 0.7 mL/min; Injection: 20 μL; Detector: UV 210 nm). Comparison of select mutants can be seen in Table 1.

TABLE 1

Enzymatic panel for the diastereoselective hydrolysis of (±)-diethyl 2-(difluoromethyl)cyclopropane-1,1-carboxylate to (±)-2-(difluoromethyl)-1-(ethoxycarbonyl)cyclopropanecarboxylic acid.

| Mutant | Conversion @ 4 hrs (%) | Product d.e. (%) | Product e.e. (%) |
|---|---|---|---|
| BsteE | 28.4 | 75.7 | 26.3 |
| T25H/L92H | 70.8 | 96.3 | 6.3 |
| +K121R | 76.1 | 95.6 | 2.1 |
| +K121Y | 82.4 | 97.1 | 1.1 |
| +K121H | 97.9 | 97.8 | 0.3 |
| +M126F | 55.2 | 94.1 | 5.8 |
| +M126V | 50.3 | 97.7 | 3.9 |
| +M126I | 59.1 | 97.8 | 3.8 |
| +M126Q | 21.9 | 97.7 | 27.2 |
| +M194L | 64.2 | 95.4 | 9.0 |
| +M194A | 53.7 | 94.2 | 0.8 |
| +L166N | 49.2 | 93.7 | 5.3 |
| +L166M | 60.3 | 98.1 | 2.4 |
| +I170N | 97.8 | 93.2 | 0.7 |
| +I170Q | 31.8 | 92.0 | 25.6 |

As variant activities drastically improved, a more rigorous activity assay was utilized to provide great resolution between highly active mutants. Expression was carried out in the same procedure to yield a 50 mL pellet. Following decantation of the pellet, cells were resuspended in 5 mL 200 mM NaHPO$_4$ buffer, pH 8. The cell suspension was sonicated (10 sec on, 10 sec off for 1 minute total) to lyse cells and centrifuged to pellet cell debris (15 min at 9000 RPM). The resulting 5 mL of clarified lysate was measured for soluble protein content using standard Bradford Commassie Protein Assay. Lysate addition was normalized by the protein measurement to result in a final concentration of 1 mg/mL total protein in 10 mL (200 mM NaHPO$_4$ buffer, pH 8) buffer solution in the 20 mL vial. 100 μL of (±)-dipropyl 2-(difluoromethyl)cyclopropane-1,1-carboxylate (final concentration of approximate 10 g diester/L) was added to each reaction (t=0 hr), and the reaction incubated at 40° C. with 250 RPM agitation with a diamond-shaped magnetic stir bar. Reaction aliquots of 500 μL were taken at 1, 3, 5, and 24.5 hours for analysis. Aliquots were combined with 3 drops of 20% HCl solution and extracted into 1 mL MTBE. The organic phase was analyzed by chiral normal phase HPLC to determine conversion and selectivity. (Column: Phenomenex Lux 3 μm Cellulose-2; 250 mm×4.6 mm; 20° C.; Mobile phase: Heptane/iPrOH/TFAA, 98.5/1.5/0.1; Flow: 0.7 mL/min; Injection: 20 μL; Detector: UV 210 nm). Comparison of select mutants can be seen in Table 2.

TABLE 2

Further enzymatic panel for the diastereoselective hydrolysis of (±)-diethyl 2-(difluoromethyl)cyclopropane-1,1-carboxylate to (±)-2-(difluoromethyl)-1-(ethoxycarbonyl)cyclopropanecarboxylic acid.

| Mutant | Conversion @ 5 hrs (%) | Product d.e. (%) | Product e.e. (%)* |
|---|---|---|---|
| BsteE | 12.8 | 91.1 | 75.2 (@42% conv.) |
| T25H/L92H | 14.4 | 100 | 55.4 (@58% conv.) |
| +K121D | 72.1 | 98.0 | 0.6 (@99.9% conv.) |
| +K121L | 93.8 | 94.3 | -3.7% (@100% conv.) |
| +K121H | 42.4 | 97.8 | 7.3 (@97% conv.) |

*as % conversion increases, % e.e. decreased toward 0%.

Example 1b: Comparison of Wild-Type and Mutant BsteE Esterases in Enzymatic Hydrolysis The new variant enzymes; including the highly-selective triple variant T25H/L92H/K121L (identified in Table 2), exhibit improved selectivity and activity over the wild-type *Bacillus stearothermophilus* esterase (Scheme 5) in producing (±)-2-(difluoromethyl)-1-(ethoxycarbonyl) cyclopropane carboxylic acid dicyclohexylamine salt, resulting in increased yield and improved processing time when applied in the following process:

Step 1: Triple variant enzyme (i.e., T25H/L92H/K121L) catalyzes selective hydrolysis of rac-cyclopropyl diethyl ester ((±)-diethyl 2-(difluoromethyl) cyclopropane-1,1-carboxylate). Rac-cyclopropyl diethyl ester was treated with an engineered *Bacillus stearothermophilus* esterase clarified lysate suspended in Sodium Phosphate buffer at pH 8 in an agitated reactor. The reaction was agitated until reaction completion under pH control to 8 by addition of 15% Sodium Bicarbonate solution resulting in selective hydrolysis to rac-DF Acid Ester with <3% production of the undesired diastereomers. The rac-DF Acid Ester was recovered from the aqueous buffer by extraction into MTBE.

Step 2: The extracted rac-DF Acid Ester is converted to the (±)-2-(difluoromethyl)-1-(ethoxycarbonyl) cyclopropane carboxylic acid dicyclohexylamine salt in MTBE:heptane, which is recovered as a solid. The high d.e. of the Step 1 monoacids allows for this recovery in a single step without reslurry or recrystallization.

The improved enzyme variant, T25H/L92H/K121L, can yield (±)-2-(difluoromethyl)-1-(ethoxycarbonyl) cyclopropane carboxylic acid dicyclohexylamine salt at approximately 80-90% in sufficient quality and chiral purity to meet the process requirements. The wild-type variant would produce an imbalanced distribution of monoacid esters not suitable for use in the process.

Scheme 5: Enzymatic synthesis of rac-Df Acid Ester by wild-type BsteE enzyme.

Scheme 6: Enzymatic synthesis of (±)-2-(difluoromethyl)-1-(ethoxycarbonyl) cyclopropane carboxylic acid dicyclohexylamine salt by BsteE variant T25H/L92H/K121L.

Example 1c: Preparation of Mutant BsteE Plasmid

Mutations were incorporated into the desired plasmid through Quikchange™ PCR amplification. DNA primers were designed corresponding to each of the desired mutations by utilizing the Agilient Quikchange Primer Design tool. PCR reactions were prepared by combining 0.5 µL DMSO, 0.5 µL of each primer at 10 µM concentration, 1 µL of the template plasmid at 50 µg/mL, 1 µL of 20 mM dNTPs (5 mM each nucleotide), 2.5 µL 10×DNA polymerase buffer, 18.5 µL Ultrapure water, 0.5 µL DNA polymerase. PCR reactions were submitted to the following temperature cycle procedure; 95° C. for 3 min, [Cycle start] 95° C. for 30 sec, 55° C. for 1 min, 68° C. for 8 min, [Repeat from "Cycle start" 15 times] 68° C. for 10 min, 4° C. HOLD. Following amplification, parental DNA was digested with 2 μL DpnI at 37° C. for 4 hours with 20 min of 80° C. heat deactivation upon completion. The 0.5 μL of the PCR product was transformed in BL21 (DE3) competent cells using the standard transformation procedure and plated onto LB+KAN (50 μg/mL) selective plates.

Example 2: Scale-Up of Diastereoselective Enzymatic Hydrolysis (±)-2a
(Major Diastereomer)

(±)-2b
(Minor Diastereomer)

The procedure of Example 1a was followed, utilizing 30 g of the diethyl ester starting material (1). The resulting material (2a) met product specifications for purity (≥ 97 area %) and diastereomer (≤1.50 area %).

Enzyme Preparation from Pilot-Scale Fermentation

Enzyme expression was achieved in a 55 L fermentation vessel using common growth and expression procedures and IPTG induction. The resulting cells (28 L at approximate 20% wet cell weight) were pelleted through a disc stack centrifuge at 10,000×g with a resonance time of 12 minutes. The cells were re-suspended by agitation in buffer at a ratio of 1:1 v/v with 50 mM NaHPO$_4$ buffer, pH 8. The cell suspension was passed twice through a homogenizer to lyse the cells. The resulting product stream was passed through a batch centrifuge at 10,000×g for 30 minutes to remove cell debris. The resulting effluent was used a the clarified enzyme solution with a measured Bradford protein concentration of 16.8 mg/mL.

Enzymatic Hydrolysis

The effluent at 16.8 mg/mL was further diluted to a protein concentration of 3 mg/mL by the addition of 50 mM NaHPO$_4$ buffer, pH 8. The resulting solution was 3 mg/mL protein in 500 mL volume of buffer at pH 7.2, and was charged to a 500 mL ChemGlass reactor with a single glass baffle. The diester substrate (25.31 g) was loaded to the reactor by pipet. Agitiation was start with a pitch blade agitator at 450 RPM. The reaction pH was constantly monitor and controlled to pH 8 by the addition of 30% w/w sodium bicarbonate. The vessel jacket temperature was set to 47° C. to achieve a reactor internal temperature of 45° C. After 40.5 hours, the reaction had achieved 99.8% conversion by HPLC and had stated 33.67 mL of base. The reaction was worked up by cooling to 25° C. 30 mL of 50% w/w HCl was added to adjust the reaction pH to 1.69 and agitated for 30 minutes. The reaction was extracted by the addition of 350 mL of MTBE. The biphasic mixture was centrifuged at 3200×g for 30 minutes to aid in separation and compress the rag layer. The organic layer was decanted and retained. The aqueous layer was back extracted with an addition 200 mL of MTBE. The resulting MTBE layers were combined and concentrated by rotovap to yield the desired monoacid mixture (25.314 g, 90.8% purity) with an approximate % PA diastereomer of 2.5% PA.

DCHA Salt Formation

DF Acid Ester (5.05 g, 0.0243 mol, 1.0 equiv.) was charged to a clean, dry, 100 mL 3-neck flask equipped with a stir bar, reflux condenser, nitrogen inlet, and temperature probe. 2.2 mL of tert-Butyl methyl ether [0.43 mL/g of DF Acid Ester] was charged and stirring was initiated. 40.8 mL of n-Heptane [8.08 mL/g of DF Acid Ester] was charged and the solution was heated to 75° C. Dicyclohexylamine (5.9 mL, 0.0294 mol, 1.2 equiv.) was slowly added drop wise over 10 minutes under nitrogen. During this period, the contents of the reaction formed a uniform slurry. After the addition was complete, the resulting slurry was stirred at 75° C. for 1 hour, and then cooled to room temperature (23° C.). The slurry was stirred at room temperature for 4 hours, and then cooled to 8° C. and held for 2 hours. The cold slurry was filtered and washed 3 times with 4.7 mL each of a cold solution of 1:1 (by volume) MTBE/heptane [total 1.5 mL/g of expected DF Acid Ester DCHA]. The filtered solids were dried at 40° C. under vacuum to give DF Acid Ester DCHA as a white powder (9.22 g, 0.73% diastereomer, 97.6 area % by HPLC, 89% yield).

| Diester (1) | | | | | DCHA Salt Formation | | | |
|---|---|---|---|---|---|---|---|---|
| GC Assay | | Enzymatic Hydrolysis | | | DF Acid Ester DCHA (2a and 2b) | | | |
| Purity | qNMR | Rxn | Acid Ester | | Purity | % d.e. | | Two-Step |
| (≥88 area %) | Wt % | Scale | % d.e. | Yield | (≥97 area %) | (≥97%) | Yield | Yield |
| 89% | 85.1% | 30 gW | 97.54% | 93.4% | 98.8% | 99.3 % | 89.3% | 83.4% |

Comparative Example 2a: Non-Enzymatic Hydrolysis of (±)-diethyl 2-(difluoromethyl)cyclopropane-1,1-carboxylate (1)

Ethanol (3.79 equiv.) and purified water (5 equiv.) were charged to a clean reactor. (±)-diethyl 2-(difluoromethyl)cyclopropane-1,1-carboxylate (1,1 equivalent) was charged to the mixture at 15-25° C. The reaction was cooled to 5° C. and tetra butyl ammonium hydroxide (1 equiv.) was added dropwise. After 2 hours of agitation, the reaction was sampled by HPLC to determine the level of hydrolysis. Further addition was tetra butyl ammonium hydroxide was performed until the remaining diester was <2% by HPLC. HCl (0.69 equiv.) in water (6.9 equiv.) was charged to the reactor at 0-10° C. to achieve a pH of ≤3. MTBE (7.4 equiv.) was charged to the reactor an agitated for 30-60 minutes at 15-25° C. The organic phase was separated and retained. The aqueous phase was back extracted with MTBE (3.18 equiv.) at 15-25° C. an 30-40 minutes of agitation. The organic layer was separated for the aqueous and combine with the previous extraction layer. The organic layer was washed with brine (3.44 equiv. water, 0.86 equiv. NaCl) and then water (4.3 equiv.). The organic layer was separated and concentrated by reduced pressure at <40° C. The reaction was cooled to 15-25° C., and DCHA (0.845 equiv.) was added. The reaction was heated to 55-59° C. under reflux for 1-2 hours. The reaction was cool to 15-25° C. and held for >8 hours. Heptane (approx. 4.4 equiv.) was added as necessary until the undesired diastereomers were <4% PA by HPLC. The resulting solid was captured by filtration and rinse with MTBE (1.5 equiv.). The solid was then repeatedly reslurried in MTBE (4.24 equiv.) followed by the same heating (55-59° C.) and cooling and filtration procedure until the undesired diastereomers were <1.5% PA by HPLC. The resulting filter cake was dried by reduced pressure to remove MTBE, resulting in the desired DCHA racemic salt (98% purity, >97% d.e., 51-58% yield).

The procedure outlined in Comparative Example 2a yields the product as a mixture of diastereomers (about 60% d.e. compound 2a to 2b) in about 51% to 56% yield. The hydrolysis cycle proceeded over a course of about 24 hours.

In contrast, the methods of the claimed invention, exemplified in Examples 1a and 2 affords the diastereoenriched product 2a in about 98% d.e. and about 85% yield. The hydrolysis cycle also proceeded over a course of about 24 hours.

Example 3: Enzymatic Resolution En Route to Drug Substance

As shown in Scheme 2, (±)-2a can be converted to or incorporated in a Drug Substance by a set of amination and resolution reactions.

An exemplary amination reaction is shown in Scheme 7, below:

Scheme 7: Amination of diastereoenriched (±)-2-(difluoromethyl)-1-(alkoxycarbonyl)cyclopropanecarboxylic acid.

Resolution of the amination product, racemic amino ester ((±)-3), may be conducted using enzymatic resolution, as shown in Scheme 8 and described in the following synthetic procedure:

Scheme 8: Enzymatic Resolution of racemic amino ester ((±)-3).

A solution of amino ester (±)-3 in acetone was mixed with an aqueous solution of sodium bicarbonate/sodium carbonate buffer. Alcalase® 2.4 L (1.3 g per g of (±)-3) was added and the mixture agitated at 40° C. After reaction completion, the enantiomer (SS-4) was removed in the aqueous layer and the product (RR-3) was extracted into MTBE. The product (RR-3) can be converted to the amino acid (RR-4) under standard saponification procedures.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, and published patent applications, and patent applications cited throughout this application are incorporated herein by reference.

We claim:

1. A method of conversion of starting material 1 to reaction product 2 according to reaction Scheme A:

Scheme A (±)
1

(±)
2 wherein $R^1$ is ($C_1$-$C_6$)alkyl;

$R^2$ is —$CF_2$H or —CH=$CH_2$; and the first enzyme is a mutant of BsteE esterase;

wherein BsteE esterase has the sequence:

AKIVPPKPFFFEAGERAVLLLHGFTGNSADVRML-GRFLESKGYTCHAPIYKGHGVPP EELVHTGPD-DWWQDVMNGYEFLKNKGYEKIAVAGLSLG-GVFSLKLGYTVPIEGIVTMCAP MYIKSEETMYEGVLEYAREYKKREGKSEEQ-IEQEMEKFKQTPMKTLKALQELIADVRDHL DLI-YAPTFVVQARHDEMINPDSANIIYNEIESPVKQ-IKWYEQSGHVITLDQEKDQLHEDIYAF LESLDW (SEQ ID NO:10); and wherein the mutant of BsteE esterase comprise the sequence ID NO: 10 having a first mutation of T25H, a second mutation of L92H, and a third mutation selected from the group consisting of C115S, C115A, K121R, K121Y, K121H, K121D, K121L, K121T, K121A, K121N, E123T, M126F, M126V, M126I, M126Q, M126N, K164S, L166N, L166M, L166I, L166T, L166A, I170N, I170Q, I170V, I170T, I170A, D172N, M194A, M194L, I195G, I195A, I195V, and K215N.

2. The method of claim 1, wherein the amount of the first enzyme is about 50 wt % to about 200 wt % as compared to the starting material in Scheme A.

3. The method of claim 1, wherein the first solvent comprises one or more organic solvents.

4. The method of claim 1, wherein the first solvent further comprises an aqueous buffer.

5. The method of claim 1, wherein the first solvent further comprises a base.

6. The method of claim 5, wherein the base is a di(alkyl)amine.

7. The method of claim 1, further comprising contacting the reaction product of reaction Scheme A with a base to obtain a salt of the reaction product.

8. The method of claim 7, wherein the base is a di(alkyl)amine.

9. The method of claim 1, wherein the diastereomeric excess of the reaction product is greater than about 90%.

10. The method of claim 6, wherein the base is a di(cycloalkyl)amine or a di(aralkyl)amine.

11. The method of claim 8, wherein the base is a di(cycloalkyl)amine or a di(aralkyl)amine.

\* \* \* \* \*

SEQUENCE LISTING

<160> NUMBER OF SEQ ID NOS: 10

<210> SEQ ID NO 1
<211> LENGTH: 750
<212> TYPE: DNA
<213> ORGANISM: Bacillus stearothermophilus

<400> SEQUENCE: 1

```
atggcgaaga ttgtcccgcc gaagccgttt ttctttgaag ccggtgaacg tgctgtcctg      60
ctgctgcatg gttttaccgg taactccgct gatgtgcgta tgctgggccg ctttctggaa     120
tccaaaggtt atacctgcca tgcgccgatt tacaagggcc acggtgtccc gccggaagaa     180
ctggtgcata cgggtccgga tgactggtgg caggatgtta tgaacggcta cgaatttctg     240
aagaacaagg gttacgaaaa gatcgcagtg gcaggtctga gcctgggcgg tgtttttcagc   300
ctgaaactgg gctataccgt tccgattgaa ggtatcgtca cgatgtgtgc accgatgtat     360
attaaaagcg aagaaaccat gtacgaaggt gtgctggaat atgctcgtga atacaaaaag     420
cgcgaaggca atctgaaga acagatcgaa caagaaatgg aaaagttcaa gcagaccccg      480
atgaaaacgc tgaaggcact gcaagaactg attgctgatg ttcgtgacca tctggatctg     540
atctatgcac cgaccttcgt ggttcaggca cgtcacgacg aaatgattaa cccggattca     600
gcgaacatca tctacaacga aatcgaatcg ccggtcaaac agatcaagtg gtacgaacaa     660
agcggtcacg tgattacgct ggaccaggaa aaagatcaac tgcatgaaga catctacgcc     720
ttcctggaaa gtctggattg gtgactcgag                                      750
```

<210> SEQ ID NO 2
<211> LENGTH: 247
<212> TYPE: PRT
<213> ORGANISM: Bacillus stearothermophilus

<400> SEQUENCE: 2

```
Met Ala Lys Ile Val Pro Pro Lys Pro Phe Phe Phe Glu Ala Gly Glu
1               5                   10                  15

Arg Ala Val Leu Leu Leu His Gly Phe Thr Gly Asn Ser Ala Asp Val
            20                  25                  30

Arg Met Leu Gly Arg Phe Leu Glu Ser Lys Gly Tyr Thr Cys His Ala
        35                  40                  45

Pro Ile Tyr Lys Gly His Gly Val Pro Pro Glu Glu Leu Val His Thr
    50                  55                  60

Gly Pro Asp Asp Trp Trp Gln Asp Val Met Asn Gly Tyr Glu Phe Leu
65                  70                  75                  80

Lys Asn Lys Gly Tyr Glu Lys Ile Ala Val Ala Gly Leu Ser Leu Gly
                85                  90                  95
```

Gly Val Phe Ser Leu Lys Leu Gly Tyr Thr Val Pro Ile Glu Gly Ile
            100                 105                 110

Val Thr Met Cys Ala Pro Met Tyr Ile Lys Ser Glu Glu Thr Met Tyr
            115                 120                 125

Glu Gly Val Leu Glu Tyr Ala Arg Glu Tyr Lys Lys Arg Glu Gly Lys
            130                 135                 140

Ser Glu Glu Gln Ile Glu Gln Glu Met Glu Lys Phe Lys Gln Thr Pro
145                 150                 155                 160

Met Lys Thr Leu Lys Ala Leu Gln Glu Leu Ile Ala Asp Val Arg Asp
                165                 170                 175

His Leu Asp Leu Ile Tyr Ala Pro Thr Phe Val Val Gln Ala Arg His
                180                 185                 190

Asp Glu Met Ile Asn Pro Asp Ser Ala Asn Ile Ile Tyr Asn Glu Ile
            195                 200                 205

Glu Ser Pro Val Lys Gln Ile Lys Trp Tyr Glu Gln Ser Gly His Val
            210                 215                 220

Ile Thr Leu Asp Gln Glu Lys Asp Gln Leu His Glu Asp Ile Tyr Ala
225                 230                 235                 240

Phe Leu Glu Ser Leu Asp Trp
                245

<210> SEQ ID NO 3
<211> LENGTH: 744
<212> TYPE: DNA
<213> ORGANISM: Bacillus stearothermophilus

<400> SEQUENCE: 3
atgggcaaaa tcgtcccgcc gaaaccgttc ttctttgaag ctggtgaacg tgctgtgctg      60
ctgctgcatg gctttcatgg caatagcgcc gacgttcgta tgctgggccg ctttctggaa     120
agcaaaggtt atacctgcca tgcaccgatt tacaaaggcc acggtgtccc gccggaagaa     180
ctggtgcata cgggtccgga tgactggtgg caggatgtca tgaacggcta cgaatttctg     240
aaaaacaaag gttacgaaaa aatcgcagtg gcaggtcata gcctgggtgg tgttttctct     300
ctgaaactgg gctataccgt tccgattgaa ggtatcgtca cgatgtgtgc accgatgtac     360
atcttatcag aagaaaccat gtacgaaggt gtgctggaat atgctcgtga atacaaaaaa     420
cgcgaaggca atcggaaga acagatcgaa caagaaatgg aaaaattcaa acagacccg      480
atgaaaacgc tgaaagcact gcaagaactg attgctgatg ttcgtgacca tctggatctg     540
atctatgcac cgaccttcgt ggttcaggca cgtcacgacg aaatgattaa cccggatagt     600
gccaacatca tctacaacga aatcgaatcc ccggtcaaac agatcaaatg gtacgaacaa     660
agtggccacg tgatcacgct ggatcaggaa aaagaccaac tgcacgaaga catttacgca     720
tttctggaat cgctggactg gtaa                                            744

<210> SEQ ID NO 4
<211> LENGTH: 247
<212> TYPE: PRT
<213> ORGANISM: Bacillus stearothermophilus

<400> SEQUENCE: 4

Met Gly Lys Ile Val Pro Pro Lys Pro Phe Phe Glu Ala Gly Glu
1               5                   10                  15

Arg Ala Val Leu Leu Leu His Gly Phe His Gly Asn Ser Ala Asp Val
                20                  25                  30

Arg Met Leu Gly Arg Phe Leu Glu Ser Lys Gly Tyr Thr Cys His Ala

-continued

```
              35                  40                  45
    Pro Ile Tyr Lys Gly His Gly Val Pro Pro Glu Glu Leu Val His Thr
    50                  55                  60
Gly Pro Asp Asp Trp Trp Gln Asp Val Met Asn Gly Tyr Glu Phe Leu
65                  70                  75                  80
Lys Asn Lys Gly Tyr Glu Lys Ile Ala Val Ala Gly His Ser Leu Gly
                85                  90                  95
Gly Val Phe Ser Leu Lys Leu Gly Tyr Thr Val Pro Ile Glu Gly Ile
            100                 105                 110
Val Thr Met Cys Ala Pro Met Tyr Ile Leu Ser Glu Glu Thr Met Tyr
        115                 120                 125
Glu Gly Val Leu Glu Tyr Ala Arg Glu Tyr Lys Lys Arg Glu Gly Lys
    130                 135                 140
Ser Glu Glu Gln Ile Glu Gln Glu Met Glu Lys Phe Lys Gln Thr Pro
145                 150                 155                 160
Met Lys Thr Leu Lys Ala Leu Gln Glu Leu Ile Ala Asp Val Arg Asp
                165                 170                 175
His Leu Asp Leu Ile Tyr Ala Pro Thr Phe Val Val Gln Ala Arg His
            180                 185                 190
Asp Glu Met Ile Asn Pro Asp Ser Ala Asn Ile Ile Tyr Asn Glu Ile
        195                 200                 205
Glu Ser Pro Val Lys Gln Ile Lys Trp Tyr Glu Gln Ser Gly His Val
    210                 215                 220
Ile Thr Leu Asp Gln Glu Lys Asp Gln Leu His Glu Asp Ile Tyr Ala
225                 230                 235                 240
Phe Leu Glu Ser Leu Asp Trp
                245
```

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 246

```
<212> TYPE: PRT
<213> ORGANISM: Bacillus stearothermophilus

<400> SEQUENCE: 10

Ala Lys Ile Val Pro Pro Lys Pro Phe Phe Phe Glu Ala Gly Glu Arg
1               5                   10                  15

Ala Val Leu Leu Leu His Gly Phe Thr Gly Asn Ser Ala Asp Val Arg
            20                  25                  30

Met Leu Gly Arg Phe Leu Glu Ser Lys Gly Tyr Thr Cys His Ala Pro
        35                  40                  45

Ile Tyr Lys Gly His Gly Val Pro Pro Glu Glu Leu Val His Thr Gly
    50                  55                  60

Pro Asp Asp Trp Trp Gln Asp Val Met Asn Gly Tyr Glu Phe Leu Lys
65                  70                  75                  80

Asn Lys Gly Tyr Glu Lys Ile Ala Val Ala Gly Leu Ser Leu Gly Gly
                85                  90                  95

Val Phe Ser Leu Lys Leu Gly Tyr Thr Val Pro Ile Glu Gly Ile Val
                100                 105                 110

Thr Met Cys Ala Pro Met Tyr Ile Lys Ser Glu Glu Thr Met Tyr Glu
        115                 120                 125

Gly Val Leu Glu Tyr Ala Arg Glu Tyr Lys Lys Arg Glu Gly Lys Ser
    130                 135                 140

Glu Glu Gln Ile Glu Gln Glu Met Glu Lys Phe Lys Gln Thr Pro Met
145                 150                 155                 160

Lys Thr Leu Lys Ala Leu Gln Glu Leu Ile Ala Asp Val Arg Asp His
                165                 170                 175

Leu Asp Leu Ile Tyr Ala Pro Thr Phe Val Val Gln Ala Arg His Asp
                180                 185                 190

Glu Met Ile Asn Pro Asp Ser Ala Asn Ile Ile Tyr Asn Glu Ile Glu
                195                 200                 205

Ser Pro Val Lys Gln Ile Lys Trp Tyr Glu Gln Ser Gly His Val Ile
                210                 215                 220

Thr Leu Asp Gln Glu Lys Asp Gln Leu His Glu Asp Ile Tyr Ala Phe
225                 230                 235                 240

Leu Glu Ser Leu Asp Trp
                245
```